United States Patent [19]

Boettcher et al.

[11] Patent Number: 5,242,925
[45] Date of Patent: Sep. 7, 1993

[54] PIPERAZINYLBENZODIOXANE DERIVATIVES

[75] Inventors: Henning Boettcher, Darmstadt; Christoph Seyfried, Jugenheim; Hartmut Greiner; Gerd Bartoszyk, both of Darmstadt, all of Fed. Rep. of Germany

[73] Assignee: Merck Patent Gesellschaft mit beschrankter Haftung, Darmstadt, Fed. Rep. of Germany

[21] Appl. No.: 933,556

[22] Filed: Aug. 24, 1992

[30] Foreign Application Priority Data

Aug. 22, 1991 [DE] Fed. Rep. of Germany ....... 4127849

[51] Int. Cl.$^5$ .................. A61K 31/495; C07D 403/14
[52] U.S. Cl. ..................................... 514/254; 544/370; 544/373; 544/377
[58] Field of Search ....................... 544/373, 370, 377; 514/254

[56] References Cited

U.S. PATENT DOCUMENTS 3,135,794 6/1964 Archer .......................... 544/373 X
4,448,777 5/1984 Heinemann et al. ........... 544/371 X
4,684,651 8/1987 Kikumoto et al. ............. 544/377 X

*Primary Examiner*—Marianne M. Cintins
*Assistant Examiner*—Michael B. Hydorn
*Attorney, Agent, or Firm*—Millen, White, Zelano & Branigan

[57] ABSTRACT

Piperazinylbenzodioxane derivatives of formula I

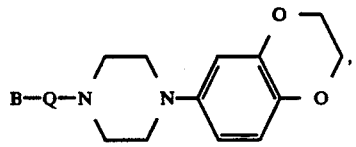

wherein B is an indol-3-yl or benzimidazol-1-yl radical which is unsubstituted or monosubstituted by CN, CO—$R^1$, $C_nH_{2n}$—$R^1$, Hal, OH, OA, O—$C_nH_{2n}$—CO—$R^1$, or $NHR^2$, and Q is $C_nH_{2n}$, or a physiologically acceptable salt thereof. The derivatives are active in the central nervous system, especially as serotonin agonists and antagonists.

16 Claims, No Drawings

PIPERAZINYLBENZODIOXANE DERIVATIVES

SUMMARY OF THE INVENTION

The invention relates to novel 1,4-benzodioxane derivatives of formula I

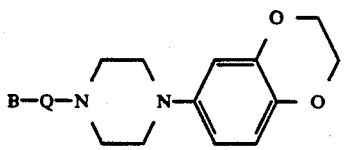

wherein
B is an indol-3-yl or benzimidazol-1-yl radical which is unsubstituted or monosubstituted by CN, CO—$R^1$, $C_nH_{2n}$—$R^1$, Hal, OH, OA, O—$C_nH_{2n}$—CO$R^1$, or NH$R^2$,
$R^1$ is OH, OA, $NH_2$, NHA, $NA_2$, NH-3-quinuclidinyl, NH—$CH_2$-3-pyridinyl, 1-piperazinyl or NH-4-(N', N''-dicarbethoxypyrazolidinyl),
$R^2$ is H, A, CO—A, CO—Ar, CO—$NH_2$, CO—NHA, CO—$NA_2$, $SO_2$—Ar or $SO_2$—A,
Q is $C_nH_{2n}$,
n is 1, 2, 3, 4, 5 or 6,
A is alkyl having 1–6 C atoms,
Ar is a phenyl radical which is unsubstituted or monosubstituted or disubstituted by A, Hal, CN, OH, and/or OA, and
Hal is F, Cl, Br or I
and to their salts.

An object of the invention is to provide novel compounds capable of being used for the preparation of drugs.

Upon further study of the specification and appended claims, further objects and advantages of this invention will become apparent to those skilled in the art.

It has been found that the compounds of formula I and their biocompatible acid addition salts posses valuable pharmacological properties. Thus, in particular, they are active on the central nervous system, especially as serotonin agonists and antagonists. They inhibit the binding of tritiated serotonin ligands to receptors in the hippocampus (Cossery et al., European J. Pharmacol. 140 (1987), 143–155). They also modify the accumulation of DOPA in the corpus striatum and the accumulation of 5-HTP in the nuclei raphes (Seyfried et al., European J. Pharmacol. 160 (1989), 31–41). They also have analgesic and hypotensive effects; thus, in catheterized, conscious, spontaneously hypertensive rats (strain: SHR/Okamoto/NIH-MO-CHB-Kisslegg; method: q.v. Weeks and Jones, Proc. Soc. Exptl. Biol. Med. 104 (1960), 646–648), the directly measured blood pressure is lowered after oral administration of the compounds. They are also useful for prophylaxis and control of the sequelae of cerebral infarction (Apoplexia cerebri) such as stroke and cerebral ischaemia.

Compounds of formula I and their biocompatible acid addition salts can therefore be used as active ingredients for anxiolytics, antidepressants, neuroleptics, and/or antihypertensives, for cerebroprotection after stroke and for prophylaxis, in Alzheimer's disease, and also as intermediates for the preparation of other pharmaceutical active ingredients.

The invention relates to the 1,4-benzodioxane derivatives of formula I and to their biocompatible acid addition salts.

The radical A is alkyl having 1, 2, 3, 4, 5 or 6 C atoms, especially 1 or 2 C atoms, preferably methyl and also ethyl, n-propyl, isopropyl, n-butyl, isotubyl, sec-butyl or tert-butyl. OA is preferably methoxy and also ethoxy, n-propoxy, isopropoxy, n-butoxy, isobutoxy, sec-butoxy or tert-butoxy. NHA is preferably methylamino and also ethylamino, n-propylamino, isopropylamino, n-butylamino, isobutylamino, sec-butylamino or tert-butylamino. $NA_2$ is preferably dimethylamino and also N-ethyl-N-methylamino, diethylamino, di-n-propylamino, diisopropylamino or di-n-butylamino.

Analogously, CO—NHA is preferably N-methylcarbamoyl or N-ethylcarbamoyl; CO—$NA_2$ is preferably N,N-dimethylcarbamoyl or N,N-diethylcarbamoyl and $SO_2$—A is preferably methylsulfonyl or ethylsulfonyl.

The radical Ar is preferably unsubstituted phenyl but can also be monosubstituted or disubstituted phenyl. If phenyl is disubstituted, it is possible for the substituents to be identical or different. Preferred substituents on the phenyl group are F, Cl, methoxy, CN, $CF_3$ or methyl. Where the phenyl radicals are substituted, the substituents are in the ortho, meta and/or paraposition, disubstituted phenyl radicals preferably being ortho- and para-substituted. Specifically, Ar is preferably phenyl, o-, m- or p-trifluoromethylphenyl, o-, m-, or p-methoxyphenyl, o-, m- or p-fluorophenyl, o-, m-or p-methylphenyl, o-, m- or p-cyanophenyl or 2,4-dimethoxyphenyl, but also o-, m- or p-ethoxyphenyl, o-, m- or p-bromophenyl, 2,3-, 2,5-, 2,6-, 3,4- or 3,5-dimethoxyphenyl, 2,3- or 3,4-methylenedioxyphenyl.

The radical B is an indol-3-yl or benzimidazol-1-yl radical which is unsubstituted or monosubstituted by one of the radicals indicated. They are preferably substituted in the 5-position or else in the 4-, 6- or 7-position. Preferred substituents on the indol-3-yl radical are $CO_2CH_3$, $CO_2H$, CN, $CONH_2$, $CH_2OH$, $H_2N$—CO—NH, $CH_3$—$SO_2$—NH and $CH_3$—CO—NH, but also OH, methoxy, ethoxy, $NH_2$, or NHA, wherein A preferably being methyl or ethyl.

The benzimidazol-1-yl radical is preferably unsubstituted, and if it is substituted the especially preferred substituents are the same as those indicated for the indol-3-yl radical.

The parameter n can be 1, 2, 3, 4, 5 or 6, preferably 1, 2 or 4.

The radical Q is preferably —$(CH_2)_4$—, furthermore —$CH_2$—, —$(CH_2)_2$ or —$(CH_2)_3$—.

$R^1$ is preferably OH, methoxy or $NH_2$, furthermore preferably ethoxy, NH—$CH_3$ or N$(CH_3)_2$.

$R^2$ is preferably CO—$CH_3$, CO—$NH_2$ or $SO_2$—$CH_3$, furthermore CO—NH—$CH_3$ or CO—N$(CH_3)_2$, but also CO-phenyl or $SO_2$-methyl.

Accordingly, the invention relates particularly to those compounds of formula I in which at least one of said radicals has one of the meanings indicated above, especially one of the preferred meanings indicated above. Some preferred groups of compounds can be expressed by the following partial formulae Ia to Ii, which correspond to formula I and in which the radicals and parameters not described in greater detail are as defined for formula I, but in which:

in Ia, B is an indol-3-yl radical substituted in the 5-position by CO—$R^1$;
in Ib, B is an indol-3-yl radical substituted in the 5-position by NH$R^2$;

in Ic, B is an indol-3-yl radical substituted in the 5-position by COOH;

in Id, B is an indol-3-yl radical substituted in the 5-position by COOCH₃;

in Ie, B is an indol-3-yl radical substituted in the 5-position by CONH₂;

in If, B is an indol-3-yl radical substituted in the 5-position by CN;

in Ig, B is an indol-3-yl radical substituted in the 5-position by CH₂OH;

in Ih, B is an indol-3-yl radical substituted in the 5-position by OA;

in Ii, B is an unsubstituted benzimidazol-1-yl radical; and in Ij, B is a benzimidazol-1-yl radical substituted in the 5-position by CO—R¹, Especially preferred compounds are those of partial formulae Ik and Iak to Iik, which correspond to partial formulae I and Ia to Ij, but in which additionally: Q is —(CH₂)₄—.

The invention further relates to a process for the preparation of 1,4-benzodioxane derivatives of formula I and their salts, characterized in that a compound of formula II

B—Q—X¹    II wherein

X¹ is X or NH₂,

X is Cl, Br, I, OH or an OH group functionally modified to form a reactive group, and B and Q are as defined, is reacted with a compound of formula III

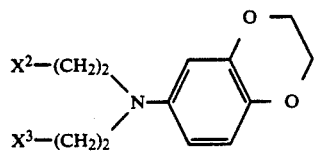

wherein

X² and X³ can be identical or different and are each X if X¹=NH₂ or are together NH in other cases, or in that a compound of formula IV

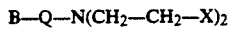
B—Q—N(CH₂—CH₂—X)₂    IV wherein

X, Q and B are as defined, is reacted with a compound of formula V

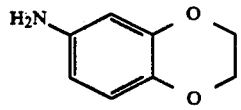

or in that a compound which has formula I except that the 1,4-benzodioxane group has been replaced by a 3,4-dihydroxyphenyl group, it also being possible, however, for the two hydroxyl groups to be present in correspondingly activated form in order to increase the reactivity, is reacted with ethanediol or a corresponding more reactive derivative to form a compound of formula I, or in that a compound which has formula I except that one or more hydrogen atoms have been replaced by one or more reducible groups and/or one or more additional C—C and/or C—N bonds is treated with a reducing agent, or in that a compound which has formula I except that one or more hydrogen atoms have been replaced by one or more solvolyzable groups is treated with a solvolyzing agent, and/or in that an OA group is optionally cleaved to form an OH group, and/or a B group is converted into another B group, and/or in that a resulting base or acid of formula I is converted into one of its salts by treatment with an acid or base.

The compounds of formula I are otherwise prepared by methods known per se, such as those described in the literature (e.g. in the standard works such as Houben-Weyl, Methoden der Organischen Chemie (Methods of Organic Chemistry), Georg-Thieme-Verlag, Stuttgart; Organic Reactions, John Wiley & Sons, Inc., New York; German Offenlegungsschrift 33 42 632), namely under reaction conditions such as those which are known and suitable for said reactions. It is also possible to make use of variants known per se, which are not mentioned in greater detail here.

If desired, the starting materials for the claimed process can also be formed in situ in such a way that they are not isolated from the reaction mixture but are immediately reacted further to give the compounds of formula I.

In the 1,4-benzodioxane derivatives of formula II, X¹ is preferably X; accordingly, in the compounds of formula III, X² and X³ are together preferably NH. The radical X is preferably Cl or Br, but it can also be I, OH or an OH group functionally modified to form a reactive group, especially alkylsulfonyloxy having 1–6 C atoms (e.g. methanesulfonyloxy) or arylsulfonyloxy having 6–10 C atoms (e.g. benzenesulfonyloxy, p-toluenesulfonyloxy, naphthalene-1- or -2-sulfonyloxy).

Accordingly, the 1,4-benzodioxane derivatives of formula I can be obtained especially by reacting compounds of the formula B—Q—Cl or B—Q—Br with 6-piperazino-1,4-benzodioxane (formula III in which X² and X³ together are an NH group; designated as IIIa hereafter).

Some of the compounds of formulae II and, in particular, III are known; the unknown compounds of formulae II and III can easily be prepared analogously to the known compounds.

Primary alcohols of the formula B—Q—OH can be obtained, e.g., by reducing the appropriate carboxylic acids or their esters. Treatment with thionyl chloride, hydrogen bromide, phosphorus tribromide or similar halogen compounds yields the corresponding halides of the formula B—Q—Hal. The corresponding sulfonyloxy compounds can be obtained from the alcohols B—Q—OH by reaction with the appropriate sulfonyl chlorides.

The iodine compounds of the formula B—Q—I can be obtained, e.g., by reacting potassium iodide with the appropriate p-toluenesulfonic acid esters. The amines of the formula B—Q—NH₂ can be prepared e.g. from the halides with potassium phthalimide or by reducing the appropriate nitriles.

The piperazine derivative IIIa can be obtained e.g. by reacting di-(2-chloroethyl)-amine with 6-amino-1,4-benzodioxane compounds of formula III (X² and X³=X in each case) can be prepared, e.g., by reducing 1,4-benzodioxanes which possess an —N(CH₂—CO₂A)₂ group in the 6-position to give the corresponding 1,4-benzodioxane derivatives which have an —N(CH$_2$CH$_2$—OH)$_2$ group in position 6, this being followed, if desired, by reaction with SOCl$_2$ or PBr$_3$.

The reaction of the compounds II and III proceeds according to methods such as those known from the literature for the alkylation of amines. The components can be melted together in the absence of a solvent, in a sealed tube or an autoclave if necessary. It is also possible, however, to react the compounds in the presence of an inert solvent. Examples of suitable solvents are hydrocarbons such as benzene, toluene or xylene; ketones such as acetone or butanone; alcohols such as methanol ethanol, isopropanol or n-butanol; ethers such as tetrahydrofuran (THF) or dioxane; amides such as dimethylformamide (DMF) or N-methylpyrrolidone; or nitriles such as acetonitrile, or else, if desired, mixtures of these solvents with one another or mixtures with water. It can be favorable to add an acid-binding agent, for example an alkali metal or alkaline earth metal hydroxide, carbonate or bicarbonate or another alkali metal or alkaline earth metal salt of a weak acid, preferably a potassium, sodium or calcium salt, or to add an organic base such as triethylamine, dimethylaniline, pyridine or quinoline, or an excess of the amine component B—Q—NH$_2$ or of the piperazine derivative of formula IIIa. The reaction time is between a few minutes and 14 days, depending on the conditions used, and the reaction temperature is between about 0° and 150°, normally between 20° and 130°.

It is also possible to obtain a compound of formula I by reacting a compound of formula B—Q—N(CH$_2$—CH$_2$—X)$_2$ (IV) with 6-amino-1,4-benzodioxane (V).

Some of the compounds of formula IV are known; the unknown compounds can easily be prepared analogously to the known compounds. Thus, compounds of formula IV can easily be prepared by reaction of B—Q—NH$_2$ with 1,2-dihaloethane, halogen preferably representing chlorine or bromine. It is also possible to obtain compounds of type IV by reaction of B—Q—Cl, B—Q—Br or B—Q—I with secondary amines of formula HN(CH$_2$—CH$_2$—X)$_2$.

The primary amine of formula V can be prepared for example starting from aniline by means of the diverse possibilities of electrophilic substitution of aromatic compounds known per se. It is also possible to convert appropriately substituted nitro compounds into the amines of formula V by reduction.

The reaction of compounds IV and V proceeds according to methods which are known from the literature for the alkylation of amines. The components can be melted with one another directly, without the presence of a solvent, if appropriate in a closed tube or in an autoclave, at normal pressure or at elevated pressure, an inert gas such as, e.g., N$_2$ being added to increase the pressure. However, it is also possible to react the compounds in the presence of an inert solvent. Suitable solvents are those mentioned previously for the reaction of II with III. The addition of an acid-binding agent to the reaction mixture can also have a favorable effect. The same bases are suitable as those previously described for the reaction of compounds II and III.

Depending on the reaction conditions chosen, the optimum reaction time is between a few minutes and 14 days, and the reaction temperature is between about 0° and 150°, usually between 20° and 130°.

Another possibility of preparing compounds of formula I consists in reacting a precursor, which contains however a 3,4-dihydroxyphenyl group instead of the 1,4-benzodioxane group, with ethanediol. Especially preferred variants of this method are however those used for example, for other preparation in which the hydroxide groups of the reactants are activated in a manner known per se.

A compound of formula I can also be obtained by treating a precursor, in which hydrogen atoms have been replaced by one or more reducible groups and/or one or more additional C—C and/or C—N bonds, with a reducing agent, preferably at temperatures of between −80° and +250°, in the presence of at least one inert solvent.

Reducible groups (groups replaceable by hydrogen) are, in particular, oxygen in a carbonyl group, hydroxyl, arylsulfonyloxy (e.g. p-toluenesulfonyloxy), N-benzenesulfonyl, N-benzyl or O-benzyl.

In principle, compounds containing only one of the abovementioned groups or additional bonds, or compounds containing two or more of the abovementioned groups or additional bonds adjacent to one another, can be converted into a compound of formula I by reduction, it being possible simultaneously to reduce substituents in the B group which are present in the starting compound. This is preferably carried out using nascent hydrogen or complex metal hydrides or by means of a Wolff-Kishner reduction or the reductions with hydrogen gas under transition metal catalysis.

Preferred starting materials for the reduction have formula VI

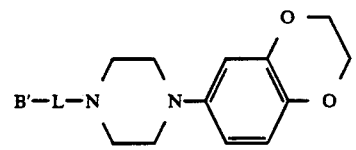

VI wherein

B′ is an indol-3-yl radical which can additionally be substituted in the 1-position by an arylsulfonyl group or a benzyl group or corresponds to an unsubstituted benzimidazol-1-yl radical, and, L is Q or a chain which corresponds to the radical Q except that one or more —CH$_2$ groups have been replaced by —CO— and/or one or more hydrogen atoms have been replaced by Cl, Br, F, SH, or OH groups, but wherein the following meanings cannot apply simultaneously: B′=B and L=Q.

In the compounds of formula VI, L is preferably —CO—(CH$_2$)$_{n-2}$—CO— [specifically —COCO—, —COCH$_2$CO—, —CO—(CH$_2$)$_2$—CO—, —CO—(CH$_2$)$_3$—CO—], —(CH$_2$)$_{n-1}$—CO— [specifically —CH$_2$—CO—, —CH$_2$CH$_2$—CO—, —(CH$_2$)$_3$—CO— or —(CH$_2$)$_4$—CO—], further examples being —CO—CH$_2$CH$_2$—, —CO—(CH$_2$)$_3$—, —CH$_2$—CO—CH$_2$CH$_2$—, —CH$_2$CH$_2$—CO—CH$_2$—, —CO—(CH$_2$)$_4$—, —CH$_2$—CO—(CH$_2$)$_3$—, —CH$_2$CH$_2$—CO—CH$_2$CH$_2$— or —(CH$_2$)$_3$—CO—CH$_2$—.

Compounds of formula VI can be prepared, e.g., by reacting 6-piperazino-benzo-1,4-dioxane with a compound of formula VII

B′—L—X$^1$    VII wherein

B′, L and X$^1$ are as defined above, under the conditions indicated above for the reaction of II with III.

If nascent hydrogen is used as the reducing agent, this can be produced, e.g., by treating metals with weak acids or with bases. Thus it is possible, e.g., to use a mixture of zinc with an alkali metal hydroxide solution or a mixture of iron with acetic acid. It is also appropriate to use sodium or another alkali metal in an alcohol such as ethanol, isopropanol, butanol, amyl or isoamyl alcohol or phenol. It is also possible to use an aluminium-nickel alloy in aqueous-alkaline solution, ethanol being added if necessary. Sodium amalgam or aluminium amalgam in aqueous-alcoholic or aqueous solution is also suitable for producing the a nascent hydrogen. The reaction can also be carried out in the heterogeneous phase, in which case it is convenient to use an aqueous phase and a benzene or toluene phase.

Other reducing agents which can be used to particular advantage are complex metal hydrides such as $LiAlH_4$, $NaBH_4$, diisobutylaluminium hydride or $NaAl(OCH_2CH_2OCH_3)_2H_2$, and diborane, catalysts such as $BF_3$, $AlCl_3$ or $LiBr$ being added if desired. Solvents which are suitable for this purpose are, in particular, ethers such as diethyl ether, di-n-butyl ether, THF, dioxane, diglyme or 1,2-dimethoxyethane, and hydrocarbons such as benzene. Solvents which are suitable for a reduction with $NaBH_4$ are primarily alcohols such as methanol or ethanol, as well as water and aqueous alcohols. Reduction by these methods is preferably carried out at temperatures of between $-80°$ and $+150°$, especially of between about $0°$ and about $100°$.

The reduction of —CO groups in acid amides (e.g., those of formula VI in which L is a —$(CH_2)_{n-1}$—CO group) to $CH_2$ groups can be carried out to particular advantage with $LiAlH_4$ in THF at temperatures of between about $0°$ and $66°$. Arylsulfonyl protecting groups located in the 1-position of the indole ring can be simultaneously eliminated by reduction. N-Benzyl groups can be eliminated by reduction with sodium in liquid ammonia.

It is also possible to reduce one or more carbonyl groups to $CH_2$ groups according to the Wolff-Kishner method, e.g., by treatment with anhydrous hydrazine in absolute ethanol, under pressure, at temperatures of between about $150°$ and $250°$. A sodium alcoholate is advantageously used as the catalyst. The reduction can also be varied according to the Huang-Minlon method by carrying out the reaction with hydrazine hydrate in a high-boiling water-miscible solvent such as diethylene glycol or triethylene glycol, in the presence of an alkali such as sodium hydroxide. The reaction mixture is normally boiled for about 3-4 hours. The water is then distilled off and the hydrazone formed is decomposed at temperatures of up to about $200°$. The Wolff-Kishner reduction can also be carried out with hydrazine in dimethyl sulfoxide at room temperature.

Moreover, it is possible to carry out certain reductions by using $H_2$ gas under the catalytic action of transition metals, such as, e.g., Raney Ni or Pd. In this way, e.g., Cl, Br, I, SH or, in certain cases, even OH groups can be replaced by hydrogen. Nitro groups can also be converted into $NH_2$ groups by catalytic hydrogenation with $Pd/H_2$ in methanol or THF.

Compounds which have formula I except that one or more H atoms have been replaced by one or more solvolyzable groups can be solvolyzed, especially hydrolyzed, to give the compounds of formula I.

The starting materials for the solvolysis can be obtained for example by reacting IIIa with compounds which have formula II ($X^1=X$) except that one or more H atoms have been replaced by one or more solvolyzable groups. Thus, in particular, 1-acylindole derivatives (which have formula I except that, in the 1-position of the Ind radical, they contain an acyl group, preferably an alkanoyl, alkylsulfonyl or arylsulfonyl group having up to 10 C atoms in each case, such as methanesulfonyl, benzenesulfonyl or p-toluenesulfonyl) can be hydrolyzed to give the corresponding indol derivatives unsubstituted in the 1-position of the indole ring, e.g. in an acidic or, preferably, neutral or alkaline medium at temperatures or between $0°$ and $200°$. Sodium, potassium or calcium hydroxide, sodium or potassium carbonate, or ammonia, is conveniently used as the base. The chosen solvents are preferably water; lower alcohols such as methanol or ethanol; ethers such as THF or dioxane; sulfones such as tetramethylene sulfone; or mixtures thereof, especially mixtures containing water. Hydrolysis can also be carried out simply by treatment with water alone, especially at the boiling point.

A compound of formula I can furthermore be converted to another compound of formula I methods known per se.

Compounds of formula I in which B is a benzimidazol-1-yl or indol-3-yl radical substituted by CO—$R^1$ can be obtained by derivatizing appropriate carboxybenzimidazol-1-yl or carboxyindol-3-yl compounds. It is possible, e.g., to esterify the acids or their reactive derivatives, such as, e.g., their acid halides or anhydrides, with appropriate alcohols or alcoholates, using the methodology known per se or one of the numerous variants. It is also possible to amidate acids, acid halides, anhydrides or esters with primary or secondary, aliphatic or cyclic amines. It is preferred to react the free carboxylic acid with the amine under the conditions of a peptide synthesis. This reaction is preferably carried out in the presence of a dehydrating agent, e.g. a carbodiimide such as dicyclohexylcarbodiimide or else N-(3-dimethylaminopropyl)-N-ethylcarbodiimide, or propanephosphonic anhydride (q.v. Angew. Chem. 92, 129 (1980)), diphenylphosphoryl azide or 2-ethoxy-N-ethoxycarbonyl-1,2-dihydroquinoline, in an inert solvent, e.g. a halogenated hydrocarbon such as methylene chloride, an ether such as THF or dioxane, an amide such as DMF or dimethylacetamide, or a nitrile such as acetonitrile, at temperatures of between about $-10$ and 40, preferably of between $0°$ and $30°$. Instead of the acid or amide, it is also possible to use reactive derivatives of these substances in the reaction, e.g., those in which reactive groups are blocked by protecting groups in an intermediate step. The acids can also be used in the form of their activated esters, which are conveniently formed in situ, e.g., by the addition of 1-hydroxybenztriazole or N-hydroxysuccinimide.

Furthermore, cyano-substituted B radicals can be hydrolyzed to give carboxyindol-3-yl or carboxybenzimidazol-1-yl radicals or carbamidoindol-3-yl or carbamidobenzimidazol-1-yl radicals.

Compounds of formula I substituted by O-alkyl can be converted by ether cleavage to the corresponding hydroxy derivatives. For example, ethers can be cleaved by treatment with dimethyl sulfide-boron tribromide complex, e.g., in toluene, ethers such as THF or dimethyl sulfoxide, or by fusion with pyridine or aniline hydrohalides, preferably pyridine hydrochloride at about $150-250°$.

The compounds of formula I can possess one or more centers of asymmetry. When prepared, they can therefore be obtained as racemates or else in the optically active form if optically active starting materials are used. When synthesized, compounds possessing two or more centers of asymmetry are generally obtained as mixtures of racemates, from which the individual racemates can be isolated in the pure form, for example by recrystallisation from inert solvents. If desired, the racemates obtained can be mechanically or chemically resolved into their optical antipodes by methods known per se. Preferably, diastereoisomers are formed from the racemate by reaction with an optically active resolving agent. Examples of suitable resolving agents are optically active acids such as the D and L forms of tartaric acid, dibenzoyltartaric acid, diacetyltartaric acid, camphorsulfonic acids, mandelic acid, malic acid or lactic acid. The different forms of the diastereoisomers can be resolved in a manner known per se, e.g. by fractional crystallization, and the optically active compounds of formula I can be liberated from the diastereoisomers in a manner known per se.

A base of formula I can be converted with an acid into the corresponding acid addition salt. Acids which produce biocompatible salts are suitable for this reaction. Thus, it is possible to use inorganic acids, e.g., sulfuric acid, hydrohalic acids such as hydrochloric acid or hydrobromic acid, phosphoric acids such as orthophosphoric acid, nitric acid and sulfamic acid, as well as organic acids, i.e., specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids and laurylsulfuric acid.

If desired, the free bases of formula I can be liberated from their salts by treatment with strong bases such as sodium or potassium hydroxide or sodium or potassium carbonate provided there are no other acid groups in the molecule. In those cases where the compounds of the formula I have free acid groups, salt formation can also be achieved by treatment with bases. Suitable bases are alkali metal hydroxides, alkaline earth metal hydroxides or organic bases in the form of primary, secondary or tertiary amines.

The invention further relates to the use of the compounds of formula I and their biocompatible salts for the manufacture of pharmaceutical preparations, especially by a non-chemical route. For this purpose, they can be converted into a suitable dosage form together with at least one excipient or adjunct and, if appropriate, in combination with one or more additional active ingredients.

The invention further relates to compositions, especially pharmaceutical preparations, containing at least one compound of formula I and/or one of their biocompatible salts. These preparations can be used as drugs in human or veterinary medicine. Possible excipients are organic or inorganic substances which are suitable for enteral (e.g., oral), parenteral or topical administration and which do not react with the novel compounds, examples of such excipients being water, vegetable oils, benzyl alcohols, polyethylene glycols, gelatin, carbohydrates such as lactose or starch, magnesium stearate, talc and petroleum jelly. Tablets, coated tablets, capsules, syrups, juices, drops or suppositories are used in particular for enteral administration, solutions, preferably oily or aqueous solutions, as well as suspensions, emulsions or implants are used for parenteral administration, and ointments, creams or powders are used for topical administration. The novel compounds can also be lyophilized and the resulting lyophilizates used, e.g., to manufacture injectable preparations.

The preparations indicated can be sterilized and/or can contain adjuncts such as lubricants, preservatives, stabilizers and/or wetting agents, emulsifiers, salts for influencing the osmotic pressure, buffer substances, colorants, taste correctors and/or flavorings. If desired, they can also contain one or more additional active ingredients, e.g., one or more vitamins.

The compounds of formula I and their biocompatible salts can be used for the therapeutic treatment of the human or animal body and for controlling diseases. They can be used for treating disorders of the central nervous system, such as nervous tension, depressions and/or psychoses, and side-effects in the treatment of hypertension (e.g., with $\alpha$-methyldopa). The compounds can also be used in endocrinology and gynecology, e.g., for the therapeutic treatment of acromegaly, hypogonadism, secondary amenorrhoea, premenstrual syndrome and undesired puerperal lactation, and also for the prophylaxis and therapy of cerebral disorders (e.g., migraine), especially in geriatrics in a manner similar to certain ergot alkaloids and for controlling the sequelae of cerebral infarction (Apoplexia cerebri), such as stroke and cerebral ischaemia.

In these treatments, the substances of the invention are normally administered analogously to known, commercially available preparations (e.g., bromocriptine, dihydroergocornine), preferably in dosages of about 0.2–500 31 mg, especially 0.2–50 mg per dosage unit. The daily dosage is preferably about 0.001–10 mg/kg of body weight. The low dosages (about 0.2 to 1 mg per dosage unit; about 0.001 to 0.005 mg/kg of body weight) are particularly suitable for use as anti-migraine preparations; dosages of 10–50 mg per dosage unit are preferred for the other indications. However, the particular dose for each individual patient depends on a very wide variety of factors, for example, the activity of the particular compound used, age, body weight, general state of health, sex, diet, time and method of administration, rate of excretion, drug combination and severity of the particular disease to which the therapy is applied. Oral administration is preferred.

In the following examples, "working-up in conventional manner" means: water is added if necessary, extraction is carried out with methylene chloride, the organic phase is separated off, dried over sodium sulfate and filtered, the filtrate is evaporated and the residue is purified by chromatography on silica gel and/or by crystallization. Temperatures above and below are given in °C. Rf values were obtained by thin layer chromatography on silica gel.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 41 27 849.6, filed Aug. 22, 1991, are hereby incorporated by reference.

EXAMPLES

Example 1

A solution of 3.6 g of 3-(4-chlorobutyl)-5-methoxycarbonylindole [obtainable by reaction of 5-methoxycarbonylindole with 4-chlorobutyryl chloride to give 3-(4-chlorobutyryl)-5-methoxy indole and subsequent reduction with diborane to give 3-(4-chlorobutyl)-5-methoxycarbonylindole] and 3.4 g of 6-piperazino-1,4-benzodioxane ("A") in 200 ml of acetonitrile is stirred at room temperature for 14 hours and worked up in the conventional manner to give 6-[4-(4-(5-methoxycarbonyl indol-3-yl)butyl)piperazino]-1,4-benzodioxane, m.p. 177–179° (dihydrochloride).

The following are obtained analogously by reaction of "A"

with 3-(4-chlorobutyl)-5-fluoroindole 6-[4-(4-(5-fluoroindol-3-yl)butyl)piperazino]-1,4-benzodioxane, m.p. 227–228° C. (Hydrochloride);

with 3-(4-bromobutyl)-5-bromoindole 6-[4-(4-(5-Bromindol-3-yl)butyl)piperazino]-1,4-benzodioxane;

with 3-(4-chlorobutyl)-5-cyanoindole 6-[4-(4-(5-cyanoindol-3-yl)butyl)piperazino]-1,4-benzodioxane;

with 3-(4-chlorobutyl)-5-chloroindole 6-[4-(4-(5-chloroindol-3-yl)butyl)piperazino]-1,4-benzodioxane, m.p. 205–207° (hydrochloride);

with 3-(4-chlorobutyl)-5-indole-carboxylic acid 6-[4-(4-(5-carboxyindol-3-yl)butyl)piperazino]-1,4-benzodioxane, m.p. 241–243° (hydrochloride);

with methyl 3-(4-chlorobutyl)-6-indolecarboxylate 6-[4-(4-(6-methoxycarbonyl-indol-3-yl)butyl)piperazino]-1,4-benzodioxane;

with 3-(3-chloropropyl)-5-fluoroindole 6-[4-(3-(5-fluoroindol-3-yl)propyl)piperazino]-1,4-benzodioxane;

with 3-(3-bromopropyl)-5-bromoindole 6-[4-(3-(5-bromoindol-3-yl)propyl)piperazino]-1,4-benzodioxane;

with 3-(3-chloropropyl)-5-cyanoindole 6-[4-(3-(5-cyanoindol-3-yl)propyl)piperazino]-1,4-benzodioxane;

with 3-(3-chloropropyl)-6-cyanoindole 6-[4-(3-(6-cyanoindol-3-yl)propyl)piperazino]-1,4-benzodioxane;

with 3-(4-chlorobutyl)-5-methoxy-indole 6-[4-(4-(5-methoxyindol-3-yl)butyl)piperazino]-1,4-benzodioxane, m.p. 107–109°;

with 3-(4-chlorobutyl)-5-hydroxy-indole 6-[4-(4-(5-hydroxyindol-3-yl)butyl)piperazino]-1,4-benzodioxane, m.p. 212–214°;

with 3-(3-chloropropyl)-indole-5-carboxylic acid 6-[4-(3-(5-carboxyindol-3-yl)propyl)piperazino]-1,4-benzodioxane;

with 3-(2-chloroethyl)-5-fluoroindole 6-[4-(2-(5-fluoroindol-3-yl)ethyl)piperazino]-1,4-benzodioxane.

Example 2

Analogously to Example 1, reaction of 1-(4-bromobutyl)benzimidazole with 6-piperazino-1,4-benzodioxane ("A") in 200 ml of acetonitrile gives 6-[4-(4-(benzimidazol-1-yl)butyl)piperazino]-1,4-benzodioxane, m.p. 247–248°.

The following are obtained analogously by reaction of "A"

with 1-(4-chlorobutyl)-5-fluorobenzimidazole 6-[4-(4-(5-fluorobenzimidazol-1-yl)butyl)piperazino]-1,4-benzodioxane;

with 1-(4-bromobutyl)-5-bromobenzimidazole 6-[4-(4-(5-bromobenzimidazol-1-yl)butyl)piperazino]-1,4-benzodioxane;

with 1-(4-chlorobutyl)-5-cyanobenzimidazole 6-[4-(4-(5-cyanobenzimidazol-1-yl)butyl)piperazino]-1,4-benzodioxane;

with 1-(4-chlorobutyl)-5-benzimidazole carboxamide 6-[4-(4-(5-carbamoylbenzimidazol-1-yl)butyl)piperazino]-1,4-benzodioxane;

with 1-(4-chlorobutyl)-5-benzimidazole carboxylic acid 6-[4-(4-(5-carboxybenzimidazol-1-yl)butyl)piperazino]-1,4-benzodioxane;

with methyl 1-(4-chlorobutyl)-5-benzimidazolecarboxylate 6-[4-(4-(5-methylcarboxybenzimidazol-1-yl)butyl)piperazino]-1,4-benzodioxane;

with 1-(3-chloropropyl)-5-fluorobenzimidazole 6-[4-(3-(5-fluorobenzimidazol-1-yl)propyl)piperazino]-1,4-benzodioxane;

with 1-(3-bromopropyl)-5-bromobenzimidazole 6-[4-(3-(5-bromobenzimidazol-1-yl)propyl)piperazino]-1,4-benzodioxane;

with 1-(3-chloropropyl)-5-cyanobenzimidazole 6-[4-(3-(5-cyanobenzimidazol-1-yl)propyl)piperazino]-1,4-benzodioxane;

with 1-(3-chloropropyl)-5-benzimidazole carboxamide 6-[4-(3-(5-carbamoylbenzimidazol-1-yl)propyl)piperazino]-1,4-benzodioxane;

with 1-(3-chloropropyl)-5-benzimidazole carboxylic acid 6-[4-(3-(5-carboxybenzimidazol-1-yl)propyl)piperazino]-1,4-benzodioxane;

with 1-(2-chloroethyl)-5-fluorobenzimidazole 6-[4-(2-(5-fluorobenzimidazol-1-yl)ethyl)piperazino]-1,4-benzodioxane;

with 1-(2-bromoethyl)-5-bromobenzimidazole 6-[4-(2-(5-bromobenzimidazol-1-yl)ethyl)piperazino]-1,4-benzodioxane;

with 1-(2-chloroethyl)-5-cyanobenzimidazole 6-[4-(2-(5-cyanobenzimidazol-1-yl)ethyl)piperazino]-1,4-benzodioxane;

with 1-(2-chloroethyl)-5-benzimidazole carboxamide 6-[4-(2-(5-carbamoylbenzimidazol-1-yl)ethyl)piperazino]-1,4-benzodioxane;

with 1-(2-chloroethyl)-5-benzimidazole carboxylic acid 6-[4-(2-(5-carboxybenzimidazol-1-yl)ethyl)piperazino]-1,4-benzodioxane;

Example 3

A mixture of 2.18 g of 3-(4-aminobutyl)-5-ethoxycarbonylindole [obtainable from 5-ethoxycarbonylindole by reaction with 4-chlorobutyryl chloride, reduction of the product to give 3-(4-chlorobutyl)-5-ethoxycarbonylindole and conversion into 3(4-phthalimidobutyl)-5-ethoxycarbonylindole] and one equivalent of 6-N,N-bis(2-chloroethyl)amino-1,4-benzodioxane ("B") in 40 ml of acetone and 40 ml of water is boiled for 24 hours and worked up in the conventional manner. 6-[4-(4-(5-ethoxycarbonylindol-3-yl)butyl)piperazino]-1,4-benzodioxane is obtained.

The following are obtained analogously by reaction of "B"

with 3-(4-aminobutyl)-5-N-methylcarbamoylindole 6-[4-(4-(5-N-methylcarbamoylindol-3-yl)butyl)-piperazino]-1,4-benzodioxane;

with 3-(4-aminobutyl)-5-N,N-dimethylcarbamoylindole 6-[4-(4-(5-N,N-dimethylcarbamoylindol-3-yl)butyl)-piperazino]-1,4-benzodioxane;

with 3-(4-aminobutyl)-6-cyanoindole 6-[4-(4-(6-cyanoindol-3-yl)butyl)piperazino]-1,4-benzodioxane;

with 3-(4-aminobutyl)-6-bromoindole 6-[4-(4-(6-bromoindol-3-yl)butyl)piperazino]-1,4-benzodioxane;

with 3-(4-aminobutyl)-5-indolyl-N-methylurea 6-[4-(4-(5-N-methylureidoindol-3-yl)butyl)piperazino]-1,4-benzodioxane;

with 3-(4-aminobutyl)-5-indolyl-N,N-dimethylurea 6-[4-(4-(5-N-N-dimethylureidoindol-3-yl)butyl)-piperazino]-1,4-benzodioxane;

with 3-(3-aminopropyl)-5-methoxyindole 6-[4-(3-(5-methoxyindol-3-yl)propyl)piperazino]-1,4-benzodioxane;

with 3-(3-aminopropyl)-6-bromoindole 6-[4-(3-(6-bromoindol-3-yl)propyl)piperazino]-1,4-benzodioxane;

with 3-(3-aminopropyl)-6-methoxyindole 6-[4-(3-(6-methoxyindol-3-yl)propyl)piperazino]-1,4-benzodioxane;

with 3-(3-aminopropyl)-4-methoxyindole 6-[4-(3-(4-methoxyindol-3-yl)propyl)piperazino]-1,4-benzodioxane;

with 3-(3-aminopropyl)-4-cyanoindole 6-[4-(3-(4-cyanoindol-3-yl)propyl)piperazino]-1,4-benzodioxane;

with 3-(3-aminopropyl)-5-ethoxyindole 6-[4-(3-(5-ethoxyindol-3-yl)propyl)piperazino]-1,4-benzodioxane;

with methyl 3-(3-aminopropyl)-indole-6-carboxylate 6-[4-(3-(6-methoxycarbonylindol-3-yl)propyl)-piperazino]-1,4-benzodioxane;

with 3-(2-aminoethyl)-4-fluoroindole 6-[4-(2-(4-fluoroindol-3-yl)propyl)piperazino]-1,4-benzodioxane;

with 3-(4-aminobutyl)-6-N-(3-quinuclidinyl)carbamoylindole 6-[4-(4-(5-N-(3-quinuclidinyl)carbamoylindol-3-yl)butyl)-piperazino]-1,4-benzodioxane, m.p. 212-219°;

with 3-(4-aminobutyl)-5-N-[(3-pyridinyl)methyl]carbamoylindole 6-[4-(4-(5-N-(3-pyridinyl)methylcarbamoylindol-3-yl)butyl)piperazino]-1,4-benzodioxane, m.p. 150-152°;

with 3(4-aminobutyl)indole-5-carboxylic acid piperazide 6-[4-(4-5-piperazinocarbonylindol-3-yl)butyl)-piperazino]-1,4-benzodioxane, m.p. 164-166°;

with 3-(4-aminobutyl)-5-N-(N',N''-di-carbethoxypyrazolidin-4-yl)carbamoylindole 6-[4-(4-5-N-(N',N''-di-carbethoxypyrazolidin-4-yl)carbamoylindol-3-yl)butyl)piperazino]-1,4-benzodioxane, m.p. 218-222°.

Example 4

Analogously to Example 3, reaction of 1-(4-aminobutyl)-5-ethoxycarbonylbenzimidazole with 6-(N,N-bis(2-chloroethyl)amino)-1,4-benzodioxane ("B") gives 6-[4(4-(5-ethoxycarbonylbenzimidazol-1-yl)butyl)piperazino]-1,4-benzodioxane.

The following are obtained analogously by reaction of with 1-(4-aminobutyl)-5-N-methylcarbamoylbenzimidazole 6-[4-(4-(5-N-methylcarbamoylbenzimidazol-1-yl)butyl)piperazino]-1,4-benzodioxane;

with 1-(4-aminobutyl)-5-N,N-dimethylcarbamoylbenzimidazole 6-[4-(4-(5-N,N-dimethylcarbamylbenzimidazol-1-yl)butyl)piperazino]-1,4-benzodioxane;

with 1-(4-aminobutyl)-6-cyanobenzimidazole 6-[4-(4-(6-cyanobenzimidazol-1-yl)butyl)piperazino]-1,4-benzodioxane;

with 1-(4-aminobutyl)-6-bromobenzimidazole 6-[4-(4-(6-bromobenzimidazol-1-yl)butyl)piperazino]-1,4-benzodioxane;

with 1-(4-aminobutyl)-5-benzimidazolyl-N-methylurea 6-[4-(4-(5-N-methyl-ureidobenzimidazol-1-yl)butyl)-piperazino]-1,4-benzodioxane;

with 1-(4-aminobutyl)-5-benzimidazolyl-N,N-dimethylurea 6-[4-(4-(5-N,N-dimethyl-ureidobenzimidazol-1-yl)butyl)piperazino]-1,4-benzodioxane;

with 1-(3-aminopropyl)-5-methoxybenzimidazole 6-[4-(3-(5-methoxy-benzimidazol-1-yl)propyl)piperazino]-1,4-benzodioxane;

with 1-(3-aminopropyl)-6-bromobenzimidazole 6-[4-(3-(6-bromobenzimidazol-1-yl)propyl)piperazino]-1,4-benzodioxane;

with 1-(3-aminopropyl)-6-methoxybenzimidazole 6-[4-(3-(6-methoxybenzimidazol-1-yl)propyl)piperazino]-1,4-benzodioxane;

with 1-(3-aminopropyl)-4-methoxybenzimidazole 6-[4-(3-(4-methoxybenzimidazol-1-yl)propyl)piperazino]-1,4-benzodioxane;

with 1-(3-aminopropyl)-4-cyanobenzimidazole 6-[4-(3-(4-cyanobenzimidazol-1-yl)propyl)piperazino]-1,4-benzodioxane;

with 1-(3-aminopropyl)-5-ethoxybenzimidazole 6-[4-(3-(5-ethoxybenzimidazol-1-yl)propyl)piperazino]-1,4-benzodioxane;

with methyl 1-(3-aminopropyl)-6-benzimidazole carboxylate 6-[4-(3-(6-methoxycarbonylbenzimidazol-1-yl)propyl)piperazino]-1,4-benzodioxane;

with 1-(2-aminoethyl)-4-fluorobenzimidazole 6-[4-(2-(4-fluorobenzimidazol-1-yl)ethyl)piperazino]-1,4-benzodioxane.

Example 5

Analogously to Example 1, reaction of 3-(4-chlorobutyl)-5-nitroindole with "A" gives 6-[4-(4-(5-nitroindol-3-yl)butyl)piperazino]-1,4-benzodioxane.

EXAMPLE 6

A solution of 4.21 g of 6-[4-(4-(5-aminoindol-3-yl)butyl)piperazino]-1,4-benzodioxane ("C") [obtainable as in Example 5] in 35 ml of THF is treated with a solution of 0.9 g of acetyl chloride in 10 ml of THF, and the mixture is stirred at 50° for 2 hours, evaporated and worked up in the conventional manner. 6-[4-(4-(5-Acetamidoindol-3-yl)butyl)piperazino]-1,4-benzodioxane is obtained.

The following are obtained analogously by reaction of "C"

with benzoyl chloride 6-[4-(4-(5-benzamidoindol-3-yl)butyl)piperazino]-1,4-benzodioxane;

with methanesulfonyl chloride 6-[4-(4-(5-methanesulfonylaminoindol-3-yl)butyl)piperazino]-1,4-benzodioxane;

with N,N-dimethylcarbamoyl chloride 6-[4-(4-(5-N,N-dimethylureidoindol-3-yl)butyl)piperazino]-1,4-benzodioxane;

with N,N-diethylcarbamoyl chloride 6-[4-(4-(5-N,N-diethylureidoindol-3-yl)butyl)piperazino]-1,4-benzodioxane;

Example 7

Analogously to Example 6, reaction of 6-[4-(4-(6-aminobenzimidazol-1-yl)butyl)piperazino]-1,4-benzodioxane ("D") with acetyl chloride gives 6-[4-(4-(6-acetamidobenzimidazol-1-yl)butyl)piperazino]-1,4-benzodioxane.

The following are obtained analogously by reaction of "D"
with benzoyl chloride 6-[4-(4-(6-benzamidobenzimidazol-1-yl)butyl)piperazino]-1,4-benzodioxane;
with methanesulfonyl chloride 6-[4-(4-(6-methanesulfonylamidobenzimidazol-1-yl)butyl)piperazino]-1,4-benzodioxane;
with N,N-dimethylcarbamoyl chloride 6-[4-(4-(6-N,N-dimethylureidobenzimidazol-1-yl)butyl)piperazino]-1,4-benzodioxane;
with N,N-diethylcarbamoyl chloride 6-[4-(4-(6-N,N-diethylureidobenzimidazol-1-yl)butyl)piperazino]-1,4-benzodioxane;

Example 8

Analogously to Example 7, reaction of 6-[4-(4-(5-aminobenzimidazol-1-yl)butyl)piperazino]-1,4-benzodioxane ("E") with acetyl chloride gives 6-[4-(4-(5-acetamidobenzimidazol-1-yl)butyl)piperazino]-1,4-benzodioxane.

The following are obtained analogously by reaction of "E"
with benzoyl chloride 6-[4-(4-(5-benzamidobenzimidazol-1-yl)butyl)piperazino]-1,4-benzodioxane;
with methanesulfonyl chloride 6-[4-(4-(5-methanesulfonylaminobenzimidazol-1-yl)butyl)piperazino]-1,4-benzodioxane;
with N,N-dimethylcarbamoyl chloride 6-[4-(4-(5-N,N-dimethylureidobenzimidazol-1-yl)butyl)piperazino]-1,4-benzodioxane;
with N,N-diethylcarbamoyl chloride 6-[4-(4-(5-N,N-diethylureidobenzimidazol-1-yl)butyl)piperazino]-1,4-benzodioxane.

Example 9

A suspension of 3.8 g of 6-[4-(4-(5-nitroindol-3-yl)butyl)piperazino]-1,4-benzodioxane in 45 ml of methanol is hydrogenated with stirring on 0.1% Pd-C at 20° and 1 bar until absorption of $H_2$ is complete. The mixture is poured into ice-water, worked up in the conventional manner and gives 6-[4-(4-(5-aminoindol-3-yl)butyl)piperazino]-1,4-benzodioxane.

The following are obtained analogously
from 6-[4-(4-(4-nitroindol-3-yl)butyl)piperazino]-1,4-benzodioxane 6-[4-(4-(4-aminoindol-3-yl)butyl)piperazino]-1,4-benzodioxane
from 6-[4-(4-(6-nitroindol-3-yl)butyl)piperazino]-1,4-benzodioxane 6-[4-(4-(6-aminoindol-3-yl)butyl)piperazino]-1,4-benzodioxane
from 6-[4-(4-(5-nitrobenzimidazol-1-yl)butyl)piperazino]-1,4-benzodioxane 6-[4-(4-(5-aminobenzimidazol-1-yl)butyl)piperazino]-1,4-benzodioxane
from 6-[4-(4-(4-nitrobenzimidazol-1-yl)butyl)piperazino]-1,4-benzodioxane 6-[4-(4-(4-aminobenzimidazol-1-yl)butyl)piperazino]-1,4-benzodioxane

Example 10

A mixture of 4.16 g of 6-[4-(4-(5-cyanobenzimidazol-1-yl)butyl)piperazino]-1,4-benzodioxane, 2.4 g of NaOH, 50 ml of $H_2O$ and 40 ml of diethylene glycol monoethyl ether is stirred at a bath temperature of 140° for 3 hours. The mixture is then cooled to room temperature, worked up in the conventional manner and gives 6-[4-(4-(5-carbamoylbenzimidazol-1-yl)butyl)piperazino]-1,4-benzodioxane.

The following are obtained analogously by partial hydrolysis of the corresponding nitriles:
6-[4-(4-(6-carbamoylbenzimidazol-1-yl)butyl)piperazino]-1,4-benzodioxane;
6-[4-(4-(5-carbamoylindol-3-yl)butyl)piperazino]-1,4-benzodioxane;
6-[4-(4-(6-carbamoylindol-3-yl)butyl)piperazino]-1,4-benzodioxane.

Example 11

A solution of 4.4 g of 6-[4-(4-(5-methoxycarbonylbenzimidazol-1-yl)butyl)piperazino]-1,4-benzodioxane in 40 ml of THF is added dropwise with stirring in an $N_2$ atmosphere at 20° to a suspension of 0.6 g of lithium aluminium hydride in 20 ml of THF. The mixture is stirred at 20° for 1 hour, decomposed with dilute sodium hydroxide solution and filtered, and the filtrate is worked up in the conventional manner and gives 6-[4-(4-(5-hydroxymethylbenzimidazol-1-yl)butyl)piperazino]-1,4-benzodioxane.

Example 12

HCl gas is passed for 2 hours into a boiling solution of 3.1 g of 6-[4-(4-(5-carboxylindol-3-yl)butyl)piperazino]-1,4-benzodioxane in 50 ml of absolute methanol. The mixture is then boiled for a further hour, worked up in the conventional manner and gives 6-[4-(4-(5-methoxycarbonylindol-3-yl)butyl)piperazino]-1,4-benzodioxane (dihydrochloride), m.p. 177–179°;

Example 13

HCl gas is passed for 2 hours into a boiling solution of 3.1 g of 6-[4-(4-(5-carboxylbenzimidazol-1-yl)butyl)piperazino]-1,4-benzodioxane in 50 ml of absolute methanol. The mixture is then boiled for a further hour, worked up in the conventional manner and gives 6-[4-(4-(5-methoxycarbonyllbenzimidazol-1-yl)butyl)piperazino]-1,4-benzodioxane.

Example 14

4.7 g of 6-[4-(4-(5-methoxycarbonylindol-3-yl)butyl)piperazino]-1,4-benzodioxane is boiled for 0.5 hour with 100 ml of 2N ethanolic KOH and worked up in the conventional manner, and gives 6-[4-(4-(5-carboxyindol-3-yl)butyl)piperazino]-1,4-benzodioxane, m.p. 241–243° (hydrochloride).

Example 15

A solution of 7.4 g of 3-[4-(N,N-bis(2-chloroethyl)aminobutyl)-5-ethoxyindole and one equivalent of 6-amino-1,4-benzodioxane in 200 ml of acetonitrile is stirred at room temperature for a period of 12 hours, worked up in the conventional manner and gives 6-[4-(4-(5-ethoxyindol-3-yl)butyl)piperazino]-1,4-benzodioxane.

The following are obtained analogously by reaction of 6-amino-1,4-benzodioxane
with 3-[4-(N,N-bis(2-chloroethyl)aminobutyl)-4-ethoxyindole 6-[4-(4-(4-ethoxyindol-3-yl)butyl)piperazino]-1,4-benzodioxane;
with 1-[4-(N,N-bis(2-chloroethyl)aminobutyl)-5-ethoxybenzimidazole 6-[4-(4-(5-ethoxybenzimidazol-1-yl)butyl)piperazino]-1,4-benzodioxane;

with 1-[4-(N,N-bis(2-chloroethyl)aminobutyl)-6-ethoxybenzimidazole 6-[4-(4-(6-ethoxybenzimidazol-1-yl)butyl)piperazino]-1,4-benzodioxane;
with 1-[3-(N,N-bis(2-chloroethyl)aminopropyl)-5-ethoxybenzimidazole 6-[4-(3-(5-ethoxybenzimidazol-1-yl)propyl)piperazino]-1,4-benzodioxane;
with 3-[2-(N,N-bis(2-chloroethyl)aminoethyl)-4-ethoxyindole 6-[4-(2-(4-ethoxyindol-3-yl)butyl)piperazino]-1,4-benzodioxane;
with 3-[2-(N,N-bis(2-chloroethyl)aminoethyl)-5-methoxyindole 6-[4-(2-(5-methoxyindol-3-yl)butyl)piperazino]-1,4-benzodioxane;

Example 16

4.7 g of 6-[4-(4-(1-benzenesulfonyl-5-bromoindol-3-yl)butyl)piperazino]-1,4-benzodioxane is boiled for 16 hours with 1.5 g of KOH in aqueous ethanol solution, worked up in the conventional manner and gives 6-[4-(4-(5-bromoindol-3-yl)butyl)piperazino]-1,4-benzodioxane.

Example 17

The following are obtained analogously to Example 9 by catalytic reduction (Pd-C/H$_2$)
from 6-[4-(4-(6-nitrobenzimidazol-1-yl)butyl)piperazino]-1,4-benzodioxane 6-[4-(4-(6-aminobenzimidazol-1-yl)butyl)piperazino]-1,4-benzodioxane
from 6-[4-(4-(7-nitrobenzimidazol-1-yl)butyl)piperazino]-1,4-benzodioxane 6-[4-(4-(7-aminobenzimidazol-1-yl)butyl)piperazino]-1,4-benzodioxane Example 18

A mixture of 3.1 g of 6-[4-(3-(5-cyanoindol-3-yl)propyl)piperazino]-1,4-benzodioxane, 2.7 g of NaOH, 100 ml of water and 50 ml of diethylene glycol monoethyl ether is stirred at a bath temperature of 140° for 3 hours. It is cooled, worked up in the conventional manner and gives 6-[4-(3-(5-carbamoylindol-3-yl)propyl)piperazino]-1,4-benzodioxane.

The following are obtained analogously by partial hydrolysis of the corresponding cyanoindoles:
6-[4-(4-(5-carbamoylindol-3-yl)butyl)piperazino]-1,4-benzodioxane, m.p. 215° (dec.);
6-[4-(4-(6-carbamoylindol-3-yl)butyl)piperazino]-1,4-benzodioxane;
6-[4-(4-(7-carbamoylindol-3-yl)butyl)piperazino]-1,4-benzodioxane.

The following Examples relate to pharmaceutical preparations containing amines of formula I or their acid addition salts:

Example A: Tablets

A mixture of 1 kg of 6-[4-(4-benzimidazol-1-yl)butyl-piperazino]-1,4-benzodioxane, 4 kg of lactose, 1.2 kg of potato starch, 0.2 kg of talc and 0.1 kg of magnesium stearate is compressed to tablets in conventional manner so that each tablet contains 10 mg of active ingredient.

Example B: Coated tablets

Tablets are formed by compression analogously to Example A and then covered in conventional manner with a coating of sucrose, potato starch, talc, tragacanth and colorant.

Example C: Capsules 2 kg of 6-[4-(4-(5-methoxyindol-3-yl)butyl)-piperazino]-1,4-benzodioxane are filled into hard gelatin capsules in conventional manner so that each capsule contains 20 mg of the active ingredient.

Example D: Ampoules

A solution of 1 kg of 6-[4-(4-(5-methoxyindol-3-yl)butyl)-piperazino]-1,4-benzodioxane in 60 l of double-distilled water is filtered under sterile conditions, filled into ampoules and lyophilized under sterile conditions and the ampoules are sealed under sterile The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1,4-benzodioxane compound of formula I

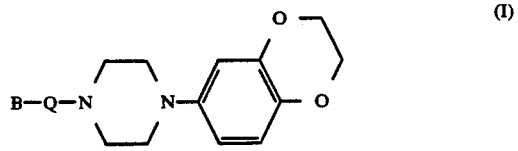

wherein
B is an indol-3-yl or benzimidazol-1-yl radical which is unsubstituted or monosubstituted by CN, CO—R$^1$, C$_n$H$_{2n}$—R$^1$, Hal, OH, OA, O—C$_n$H$_{2n}$—CO—R$^1$, or NHR$^2$;
R$^1$ is OH, OA, NH$_2$, NHA, NA$_2$, NH-3-quinuclidinyl, NH-CH$_2$-3-pyridinyl, 1-piperazinyl or NH-4-(N',N''-dicarbethoxypyrazolidinyl);
R$^2$ is H, A, CO—A, CO—Ar, CO—NH$_2$, CO—NHA, CO—NA$_2$, SO$_2$—Ar or SO$_2$—A;
Q is C$_n$H$_{2n}$;
n is 1, 2, 3, 4, 5 or 6;
A is alkyl having 1-6 C atoms;
Ar is a phenyl radical which is unsubstituted, or monosubstituted or disubstituted by A, Hal, CN, OH and/or OA; and
Hal is F, Cl, Br or I;
or a physiologically acceptable salt thereof.

2. A compound according to claim 1, wherein said compound is:
a) 6-[4-(4-(benzimidazol-1-yl)butyl)piperazino]-1,4-benzodioxane or a physiologically acceptable salt thereof;
b) 6-[4-(4(5-methoxyindol-3-yl)butyl)piperazino]-1,4-benzodioxane or a physiologically acceptable salt thereof; or
c) 6-[4-(4(5-carbamoylindol-3-yl)butyl)piperazino]-1,4-benzodioxane or a physiologically acceptable salt thereof.

3. A compound according to claim 1, wherein B is indol-3-yl substituted in the 5-position by CO—R$^1$.

4. A compound according to claim 1, wherein B is indol-3-yl substituted in the 5-position by NHR$^2$.

5. A compound according to claim 1, wherein B is indol-3-yl substituted in the 5-position by COOH.

6. A compound according to claim 1, wherein B is indol-3-yl substituted in the 5-position by COOCH$_3$.

7. A compound according to claim 1, wherein B is indol-3-yl substituted in the 5-position by CONH$_2$.

8. A compound according to claim 1, wherein B is indol-3-yl substituted in the 5-position by CN.

9. A compound according to claim 1, wherein B is indol-3-yl substituted in the 5-position by $CH_2OH$.

10. A compound according to claim 1, wherein B is indol-3-yl substituted in the 5-position by OA.

11. A compound according to claim 1, wherein B is unsubstituted benzimidazol-1-yl.

12. A compound according to claim 1, wherein B is benzimidazol-1-yl substituted in the 5-position by $CO-R^1$.

13. A compound according to claim 1, wherein Q is $-(CH_2)_4-$.

14. A pharmaceutical composition comprising a compound according to claim 1 and a pharmaceutically acceptable carrier.

15. A pharmaceutical composition according to claim 14, wherein said compound is present in an amount of 0.2–500 mg.

16. A pharmaceutical composition according to claim 14, wherein said compound is present in an amount of 0.2–50 mg.

* * * * *